United States Patent
Wadman

(10) Patent No.: US 8,077,319 B2
(45) Date of Patent: Dec. 13, 2011

(54) APPARATUS AND A METHOD FOR OBSERVING THE SURFACE OF A SAMPLE

(75) Inventor: Sipke Wadman, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 300 days.

(21) Appl. No.: 12/443,737

(22) PCT Filed: Sep. 28, 2007

(86) PCT No.: PCT/IB2007/053943
§ 371 (c)(1),
(2), (4) Date: Mar. 31, 2009

(87) PCT Pub. No.: WO2008/041162
PCT Pub. Date: Apr. 10, 2008

(65) Prior Publication Data
US 2010/0091291 A1    Apr. 15, 2010

(30) Foreign Application Priority Data
Oct. 5, 2006    (EP) ..................... 06121782

(51) Int. Cl.
*G01N 21/47* (2006.01)
(52) U.S. Cl. ...................................... 356/446
(58) Field of Classification Search .................. None
See application file for complete search history.

(56) References Cited

U.S. PATENT DOCUMENTS

| | | | |
|---|---|---|---|
| 4,360,275 A | 11/1982 | Louderback | |
| 4,575,244 A | 3/1986 | Kaffka et al. | |
| 4,815,858 A | 3/1989 | Snail | |
| 5,309,339 A | 5/1994 | Webb | |
| 5,485,263 A * | 1/1996 | Bjorner et al. | 356/4.01 |
| 6,018,396 A | 1/2000 | Rapaport et al. | |
| 6,128,073 A | 10/2000 | Henzler et al. | |
| 6,249,751 B1 | 6/2001 | Asaba et al. | |
| 6,424,413 B1 | 7/2002 | Weber et al. | |
| 6,631,000 B1 | 10/2003 | Schwarz | |
| 6,788,413 B2 | 9/2004 | Torfs et al. | |
| 2003/0210393 A1 | 11/2003 | Vaez-Iravani et al. | |
| 2005/0068537 A1 | 3/2005 | Han et al. | |
| 2006/0066873 A1 | 3/2006 | Hill | |

FOREIGN PATENT DOCUMENTS

| | | |
|---|---|---|
| WO | 0037923 A1 | 6/2000 |
| WO | 2004077032 A1 | 9/2004 |
| WO | 2004077033 A1 | 9/2004 |
| WO | 2006038196 A1 | 4/2006 |

OTHER PUBLICATIONS

R. Rykowski et al, "Imaging Sphere Enables Rapid Source Intensity Mapping", Photonics Spectra, London, GB, vol. 39, No. 9, Sep. 2005, pp. 64-68.

* cited by examiner

*Primary Examiner* — Michael A Lyons
*Assistant Examiner* — Amanda Merlino

(57) ABSTRACT

An apparatus for observing the appearance of the surface (2) of a sample (1), comprising a light source (11) for illuminating said surface (2) from a predetermined direction and means for observing the surface (2). The means of observing the surface (2) comprise a number of substantial flat mirrors (8) located in different directions with respect to said surface (2). The means furthermore comprise an optical system (6,14) for observing said flat mirrors (8). Each flat mirror (8) reflects an image of the surface (2) of the sample (1) to the image receiving part (6) of the optical system (6,14).

10 Claims, 2 Drawing Sheets

APPARATUS AND A METHOD FOR OBSERVING THE SURFACE OF A SAMPLE

Figure 1:
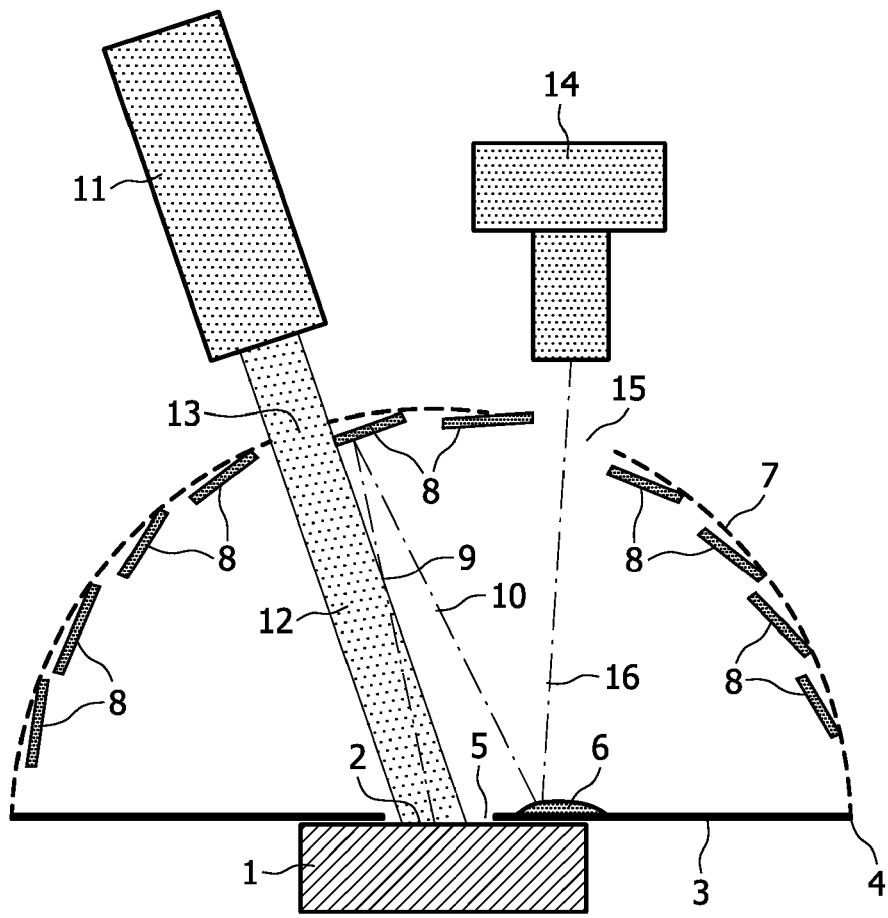

The invention is related to an apparatus for observing the appearance of the surface of a sample, comprising a light source for illuminating said surface from a predetermined direction and means for observing the surface.

The expression appearance is used in this description for each combination of aspects and/or properties of the surface of the sample and the perception of the observer of it, including the relief of the surface, the color of the surface, the light reflecting and light absorbing properties of the surface, etc. Observing is a general expression, it may include inspecting and/or recording and/or analyzing of the appearance of the surface.

In order to observe the appearance of the surface of a sample, the surface can be viewed from a certain direction, whereby a light beam is directed to the surface from another direction. Thereby, different information about the surface can be obtained, depending on the direction and intensity and color of the light and on the direction of viewing towards the surface. The observed appearance may include the texture and/or relief or protrusions or projections of the surface such as hair on the skin and, in case the surface itself is more or less translucent, the texture and/or color and/or morphology underneath the surface, i.e. the sub-surface. The observation can be recorded and/or analyzed.

A non-contact and non-perturbing monitoring technique is useful in many areas of technology to determine surface and/or sub-surface morphology. Furthermore, the type and density of material defects or other features, which have a geometric shape, can be characterized using this technique. Another use of this technique is the analysis of the characteristics and condition of human skin. It is also possible to make use of the apparatus for the calibration of the optical properties of surfaces that appear on aerial or space photography of the earth under different sun illuminations and viewing angles. For that purpose, areas of the surface of the earth, for example different kind of soil, road sealing or vegetation, can be observed by means of the apparatus, and the observations can be compared with photographs of the surface of the earth.

In particular when details of the morphology are to be analyzed, it is desired to make observations of the appearance of the surface from different directions, whereby the light source also may illuminate the surface from one or more predetermined directions (different angles with respect to the plane of the surface).

In particular when the surface of a relative large object has to be observed, for example a piece of the skin of a human body, it is not possible to place the sample inside the apparatus. In that case, the apparatus should be placed on or against the sample or a part of the sample, whereby the location of the surface to be observed is at the outer side of the apparatus.

An object of the invention is an apparatus for observing the appearance of the surface of a sample, comprising a light source for illuminating said surface from a predetermined direction, whereby the surface is observed from many different directions simultaneously, so that an analysis of the sample can be based on one observation.

Another object of the invention is an apparatus for observing the appearance of the surface of a sample, comprising a light source for illuminating said surface from a predetermined direction, whereby the surface is observed from different directions simultaneously, and whereby the sample can be located at the outer side of the apparatus.

To accomplish with one or both of these objects, the means of observing the surface comprise a number of substantial flat mirrors located in different directions with respect to the surface to be observed and an optical system for observing said flat mirrors, whereby each flat mirror reflects an image of the surface of the sample to the image receiving part of the optical system, i.e. a lens or mirror or the like. Thereby, the location of the flat mirrors may be fixed or adjustable. The mirrors are substantially flat, i.e. they are flat or they deviate a little from the flat shape in order to enlarge or reduce the image that they reflect towards the image receiving part of the optical system. Therefore, the mirrors may be a little convex or concave. Nevertheless, in this description they will be indicated as flat mirrors.

In a preferred embodiment, the flat mirrors are located at substantially equal distances from the location of the surface to be observed, i.e. near the surface of an imaginary spherical dome above the location of the surface, whereby that location is in the center of the dome. Thereby, the flat mirrors can be located along a line, i.e. a part of a circle at the surface of the imaginary dome, or the flat mirrors can be located in a grid at said surface, i.e. distributed over the surface of the imaginary dome. All other distributions of the locations of the flat mirrors are possible.

Preferably, the flat mirrors are located at substantially equal distances from the image receiving part of the optical system, i.e. a lens or mirror or the like that receives the images that are reflected by the flat mirrors. In case the flat mirrors are located near the surface of an imaginary spherical dome as described above, then the image receiving part of the optical system is, just like the surface to be observed, located near the center of that dome. Thereby, the optical system is observing the surface through different mirrors from the same distance, so that the images are comparable.

In a preferred embodiment, the image receiving part of the optical system and the surface to be observed are located near each other, whereby the average distance between the location of the surface to be observed and the flat mirrors is more than ten times, preferably more than fifteen times, the distance between the location of the surface to be observed and the location of the image receiving part of the optical system. When the location of the surface to be observed and the location of the lens or mirror that receives the image of the surface are close to each other, all flat mirrors can be located at substantial equal distances from both said locations, whereby the optical system observes the surface through all flat mirrors from substantially the same distance.

The optical system may be provided with a convex lens, a so called fish-eye lens or wide angle lens, in order to receive all images of the surface from the different directions. However, in a preferred embodiment, the image receiving part of the optical system is a substantially spherical mirror, preferably a convex mirror, whereby the flat mirrors reflect images of the surface towards the spherical mirror, so that different images of the surface can be observed through said spherical mirror. The reflecting surface of such mirror has substantially the shape of a part of a globe, so that, when looking to that mirror, a wide angle view of the surrounding of the mirror can be seen.

By making use of a mirror for receiving the images, the apparatus can be designed in such manner that the light source as well as the flat mirrors as well as the optical system including the mirror are located at one side of a plane through the location of the surface to be observed. Thereby, the apparatus can be designed in such manner that it can be placed against the sample, or the sample can be placed against the apparatus, so that a piece of the surface of a relatively large sample can be observed. The apparatus can be designed as a hand-held device that can be placed on the skin of a human body.

Preferably, five or more flat mirrors are present, and more preferably, more than eight mirrors are present, so that details of the surface to be observed are seen by the optical system simultaneously from many directions in order to make a throughout analysis of the surface.

In a preferred embodiment, the optical system comprises a camera for recording a representation of the surface, which representation comprises many images of the surface to be observed, taken from different directions, whereby the camera as well as the light source has a fixed location.

Preferably, location of the light source is adjustable, so that the surface of the sample can be illuminated from different predetermined directions, i.e. the incident light beam hits the surface of the sample at different angles. Thereby, the camera can record representations whereby the surface is illuminated differently, so that more information of the surface can be obtained.

In a preferred embodiment, the apparatus comprises a spherical screen being located in front of the flat mirrors, which screen is provided with one or more openings through which a light beam can pass, and with an opening through which the image receiving part of the optical system can be observed. The spherical screen can be a removable dome made of diffuse material. Thereby, the apparatus can additionally be used as a scatterometer, being an apparatus that is for example described in WO-A-2004/077032, which is also an apparatus for analyzing properties of a surface. Thereby, instead of images of the surface of the sample, the light reflection (radiation) in different directions from the surface can be recorded, which is another technique for detecting and analyzing aspects and properties of the surface of the sample. The dome can also be partly diffuse, so that the camera can take one picture comprising a number of images of the surface to be observed, seen through the flat mirrors, and one or more images showing the radiation of the surface to be observed in predetermined directions towards the diffuse portions of the spherical screen.

Preferable, the spherical screen is made of transparent material which is coated with a material that can be made diffuse on electronic command. Thereby, the spherical screen can be completely be provided with said coating, so that the apparatus can be used as a scatterometer as well as be used to observe the surface from different directions as described above. In a preferred embodiment, the coating is applied in one or more portions of the screen, resulting in a dome that can be, on electronic command, provided with diffuse areas and transparent areas.

Coating that can be made diffuse or diffuse on electronic command is known, for example known as polymer-dispersed liquid crystals (PDLC material). By changing the orientation of the liquid crystal molecules with an electric field, the degree of transparence of the material can be varied.

The invention is also related to a method for observing the appearance of the surface of a sample, whereby a light source is illuminating said surface from a predetermined direction while the surface is observed from another direction, whereby the surface is observed through a number of substantial flat mirrors located in different directions with respect to said surface, and whereby each flat mirror reflects an image of the surface of the sample to the image receiving part of an optical system that observes said surface, preferably being a convex spherical mirror.

Figure 2:
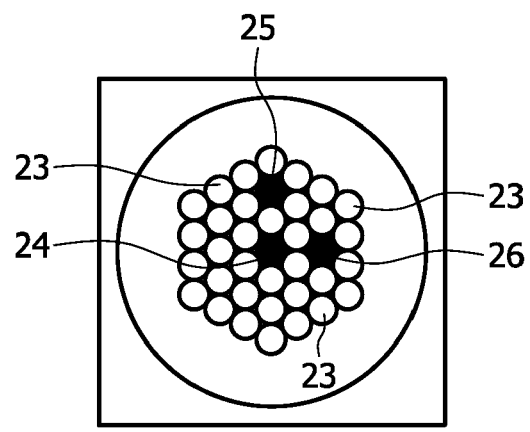
Figure 3:
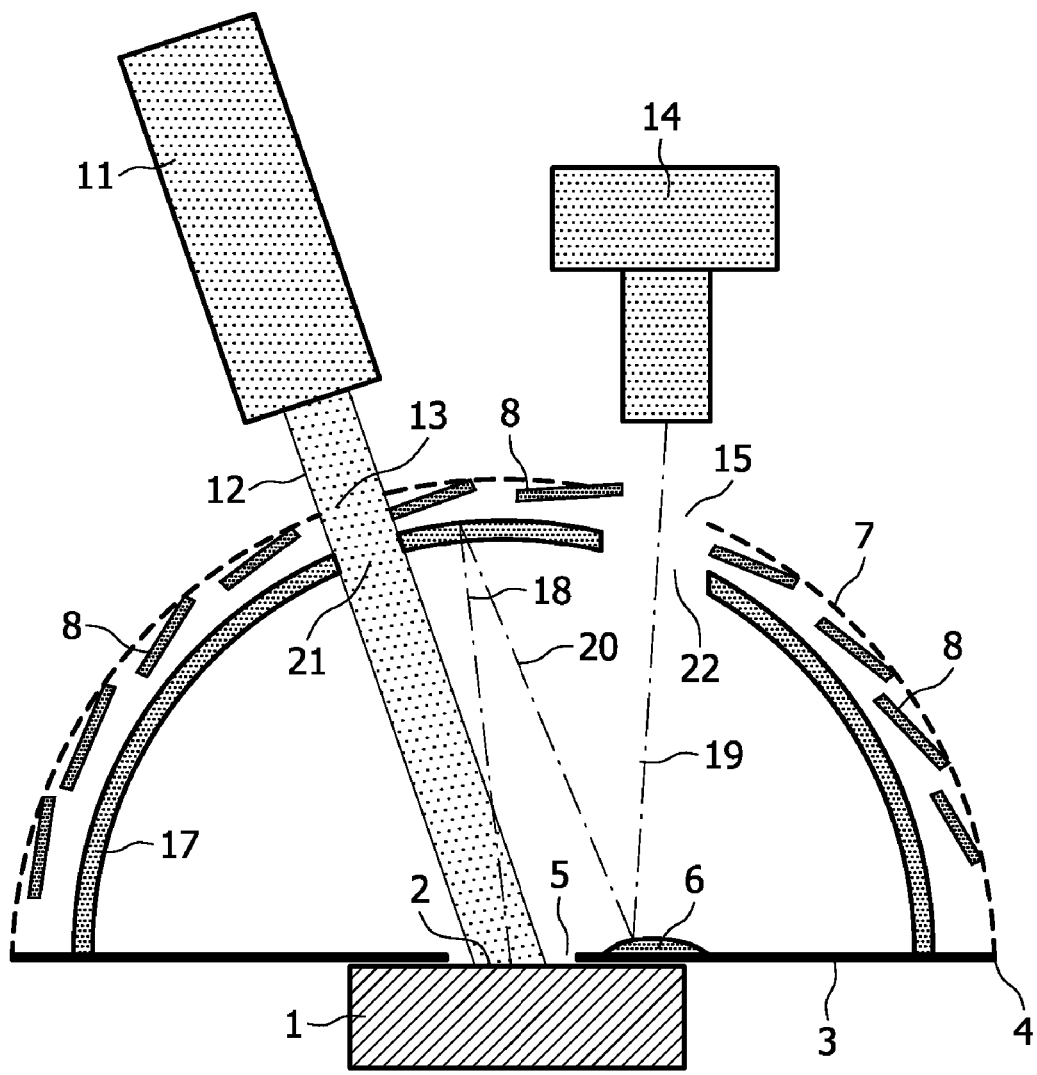

The invention will now be further elucidated by means of a description of two embodiments of an apparatus for observing the appearance of the surface of a sample, whereby reference is made to the drawing comprising three diagrammatic figures, whereby:

FIG. 1 shows the first embodiment;
FIG. 2 represent a picture recorded by the camera; and
FIG. 3 shows the second embodiment, whereby a spherical screen is present.

The three figures are only schematic and diagrammatic representations, showing only parts of the apparatus that are relevant for the elucidation of the invention. When describing the two embodiments, similar parts are indicated in the figures with the same reference numerals.

FIG. 1 shows the principle of the first embodiment of the apparatus in a schematic sectional view. It represents diagrammatically a sample 1 having a surface 2 to be observed in order to record and analyze that surface 2. The sample 1 is located underneath the base plate 3 of the apparatus for observing the surface 2. The base plate 3 has a circular outer edge 4 and a central opening 5. The surface 2 is located in the opening 5. A convex spherical mirror 6 is present on the base plate 3 and is located close to the opening 5. The circular edge 4 of the base plate 3 is connected to a half-spherical frame that is indicated with dashed line 7. The frame 7 carries a number of flat mirrors 8, which mirrors 8 are distributed over the inner surface of the frame 7. Each flat mirror 8 is positioned in such manner that it reflects an image of the surface 2 of the sample 1 towards the convex mirror 6, as is indicated with dash-dot-lines 9,10.

The surface 2 is illuminated by means of a light source 11, which light source 11 is located outside the frame 7. Light source 11 directs its light beam 12 (indicated with two dashed lines) through an opening 13 in the frame 7 at a location where no mirror 8 is present. Furthermore, a camera 14 is present outside the frame 7, which camera 14 is directed towards the convex mirror 6 through an opening 15 in the frame 7 at a location where no mirror 8 is present. The viewing direction of the camera 14 is indicated with dash-dot-line 16.

In the described apparatus, the camera 14 can take a picture as is shown in FIG. 2. The picture comprises a number of images 23 of the surface 2 of sample 1, whereby each image 23 is seen through one of the flat mirrors 8, and therefore from another direction. An analysis of the surface 2 can be made based on the picture comprising the different images 23 shown in FIG. 2. In the picture of FIG. 2 are three locations where no image 23 is present. At location 24 is a first opening in the frame 7 where no mirror 8 is present, through which opening the surface 2 can be illuminated by the light source 11 by means of a beam perpendicular to the surface 2. At location 25 is an opening in the frame 7 for illuminating the surface 2 under a certain angle. And at location 26 is an opening in the frame 7 through which opening the camera 14 has taken the picture. As an alternative, it is also possible to install an array of small light sources positioned between the flat mirrors, whereby the light sources can be switched on and off individually.

FIG. 3 shows the same apparatus as is shown in FIG. 1, however, a removable half-spherical screen 17 is present in front of the frame 7 and the mirrors 8. The screen 17 is made of diffusing material, so that the reflection of the beam 12 of the light source 11 is projected on the screen 17. Thereby, the convex mirror 6 reflects the appearance of the inner surface of the screen 17 to the camera 14, so that the picture taken by the camera 14 shows substantially the appearance of the whole screen 17. Therefore, the taken picture comprises the reflected radiation of the surface 2 in almost all directions. Dash-dot-line 18 represents such radiation in one direction and the color and intensity of that radiation is seen by the camera 14 through the convex mirror 6, as is indicated by the dash-dot-lines 19 and 20. Screen 17 has an opening 21, through which opening 21 the light beam 12 can pass, and an opening 22 so that the camera 14 can see the convex mirror 6. Based on the appearance of the inner surface of the screen 17, a further analysis of the surface 2 of the sample 1 can be made.

The two embodiments as described above are only examples of the apparatus according to the invention; many other embodiments are possible.

The invention claimed is:

1. An apparatus for observing the appearance of the surface (2) of a sample (1), comprising:
    a light source (11) for illuminating said surface (2) from a predetermined direction and
    means for observing the surface (2) comprising:
        a plurality of substantial flat mirrors (8) located in different directions with respect to said surface (2) and
        an optical system (6,14) for observing said flat mirrors (8), whereby each flat mirror (8) reflects an image of the surface (2) of the sample (1) to an image receiving part (6) of the optical system (6,14), and
        a spherical screen (17) located in front of the flat mirrors (8), wherein the screen (17) is provided with one or more openings (21) through which a light beam (12) can pass, and with an opening (22) through which the image receiving part (6) of the optical system (6,14) can be observed.

2. An apparatus as claimed in claim 1, wherein the flat mirrors (8) are located at substantially equal distances from a location of the surface (2) to be observed.

3. An apparatus as claimed in claim 1, wherein the flat mirrors (8) are located at substantially equal distances from the image receiving part (6) of the optical system (6,14).

4. An apparatus as claimed in claim 2, wherein the image receiving part (6) of the optical system (6,14) and the surface (2) to be observed are located near each other, whereby an average distance between the location of the surface (2) to be observed and the flat mirrors (8) is more than ten times the distance between the location of the surface (2) to be observed and the image receiving part (6) of the optical system (6,14).

5. An apparatus as claimed in claim 1, wherein the image receiving part of the optical system (6,14) is a spherical mirror (6), whereby the flat mirrors (8) reflect images (23) of the surface (2) towards the spherical mirror (6), so that different images (23) of the surface (2) can be observed through said spherical mirror (6).

6. An apparatus as claimed in claim 1, wherein at least five flat mirrors (8) are present.

7. An apparatus as claimed in claim 1 wherein the optical system comprises:
    a camera (14) for recording a representation of the surface (2), comprising images (23) of the surface (2) to be observed.

8. An apparatus as claimed in claim 2, wherein the location of the light source (11) is adjustable, so that the surface (2) of the sample (1) can be illuminated from different predetermined directions.

9. An apparatus as claimed in claim 1, wherein the spherical screen (17) is made of transparent material which is coated with a material that can be made diffuse on electronic command.

10. A method for observing the appearance of the surface (2) of a sample (1), comprising:
    illuminating said surface (2) from a predetermined direction;
    observing the surface (2) from another direction wherein the surface (2) is observed through a plurality of substantial flat mirrors (8) located in different directions with respect to said surface (2), wherein each flat mirror (8) reflects an image (23) of the surface (2) of the sample (1) to an image receiving part (6) of an optical system and a spherical screen (17) located in front of the flat mirrors (8), wherein the screen (17) is provided with one or more openings (21) through which a light beam (12) can pass, and with an opening (22) through which the image receiving part (6) of the optical system can be observed.

* * * * *